United States Patent
Bryans et al.

(10) Patent No.: US 7,141,606 B2
(45) Date of Patent: Nov. 28, 2006

(54) GABAPENTIN ANALOGUES FOR SLEEP DISORDERS

(75) Inventors: Justin Stephen Bryans, Balsham (GB); Leonard Theodore Meltzer, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 256 days.

(21) Appl. No.: 10/297,827

(22) PCT Filed: May 18, 2001

(86) PCT No.: PCT/US01/16343

§ 371 (c)(1),
(2), (4) Date: Dec. 11, 2002

(87) PCT Pub. No.: WO02/00209

PCT Pub. Date: Jan. 3, 2002

(65) Prior Publication Data

US 2003/0212133 A1 Nov. 13, 2003

Related U.S. Application Data

(60) Provisional application No. 60/214,171, filed on Jun. 26, 2000.

(51) Int. Cl.
- A61K 31/21 (2006.01)
- A61K 31/195 (2006.01)
- A61K 31/19 (2006.01)

(52) U.S. Cl. ............ 514/511; 514/561; 514/572; 514/530; 562/503

(58) Field of Classification Search ............ 514/511, 514/561, 572, 530; 562/503
See application file for complete search history.

(56) References Cited

U.S. PATENT DOCUMENTS

| | | | |
|---|---|---|---|
| 4,024,175 A | | 5/1977 | Satzinger et al. |
| 4,087,544 A | | 5/1978 | Satzinger et al. |
| 5,084,479 A | | 1/1992 | Woodruff |
| 5,510,381 A | | 4/1996 | Pande |
| 5,929,065 A | * | 7/1999 | Lancel ............ 514/188 |
| 6,020,370 A | * | 2/2000 | Horwell et al. ........ 514/511 |
| 6,197,819 B1 | | 3/2001 | Silverman et al. |
| 6,306,910 B1 | | 10/2001 | Magnus et al. |
| 6,372,792 B1 | * | 4/2002 | Chouinard ............ 514/561 |
| 6,436,974 B1 | * | 8/2002 | Belliotti et al. ........ 514/364 |
| 6,689,906 B1 | * | 2/2004 | Bryans et al. ........ 562/503 |
| 2002/0004528 A1 | * | 1/2002 | Magnus et al. ........ 514/561 |
| 2003/0004129 A1 | * | 1/2003 | Bountra et al. ........ 514/46 |

FOREIGN PATENT DOCUMENTS

| | | | |
|---|---|---|---|
| WO | WO97/33859 | * | 9/1997 |
| WO | 9921824 | | 5/1999 |
| WO | WO99/21824 | * | 5/1999 |
| WO | 0002546 | | 1/2000 |
| WO | WO00/02546 | * | 1/2000 |
| WO | 0142190 | | 6/2001 |

OTHER PUBLICATIONS

Rao et al., "Gabapentin-Augments Whole Blood Serotonin in Healthy Young Men", J. Neural Transmission, 73:2, 1988, pp. 129-134; XP002132906.

Placidi et al., "[Poster session V: Clinical Efficacy; Pediatric Epilepsy; Genetics and Development][5.037]Effect of Chronic Treatment With Gabapentin on Nocturnal Sleep in Epilepsy", American Epilepsy Society, Annual Meeting, abstract, 1997; XP-002132907.

Karam-Hage and Brower, "Gabapentin is Helpful for Insomnia in Alcohol-Dependent Patients During Early Recovery", Alcoholism Clinical and Exp. Res., 23:5, 1999, abstract, p. 81A; XP-002132908.

Field et al., "Gabapentin (neurontin) and S-(+)-3-isobutylgaba represent a novel class of selective antihyperalgesic agents", Brit. J. of Pharm., 121:8, 1997, pp. 1513-1522; XP-002043785.

Rodenbeck et al., "Alterations of the Sleep Stage Structure as a Feature for GABAergic Effects of a Valerian-Hop Preparation in Patients with Psychophysiological Insomnia", Somnologie, 1998; 2, 26-31.

* cited by examiner

*Primary Examiner*—Vickie Kim
(74) *Attorney, Agent, or Firm*—Mehdi Ganjeizadeh; Charles W. Ashbrook; Matthew J. Russo

(57) ABSTRACT

The invention provides a new use of compounds for formula 1 or 1A or a pharmaceutically acceptable salt thereof. The compounds are useful in the treatment of insomnia and related disorders.

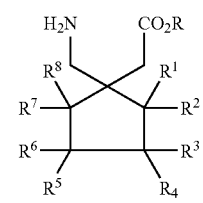

(1)

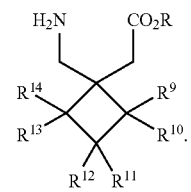

(1A)

3 Claims, No Drawings

GABAPENTIN ANALOGUES FOR SLEEP DISORDERS

This application is a §371 filing of PCT/US01/16343 filed May 18, 2001, which claims benefit of U.S. Provisional Application 60/214,171 filed Jun. 26, 2000; the entire contents of each of which are hereby incorporated herein by reference.

BACKGROUND OF THE INVENTION

Compounds of formula

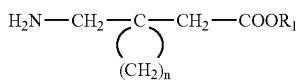

wherein $R_1$ is hydrogen or a lower alkyl radical and n is 4, 5, or 6 are known in U.S. Pat. No. 4,024,175 and its divisional U.S. Pat. No. 4,087,544. The uses disclosed are: protective effect against cramp induced by thiosemicarbazide; protective action against cardiazole cramp; the cerebral diseases, epilepsy, faintness attacks, hypokinesia, and cranial traumas; and improvement in cerebral functions. The compounds are useful in geriatric patients. The patents are hereby incorporated by reference.

U.S. patent application Ser. No. 09/485,382 filed Feb. 8, 2000, covers compounds of formulas 1 and 1A below. The application discloses various utilities for the compounds. This is incorporated by reference.

Compounds of Formula I

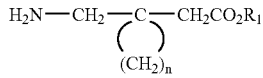

I wherein $R_1$ is hydrogen or lower alkyl and n is an integer of from 4 to 6, and the pharmaceutically acceptable salts thereof and compounds of Formula II

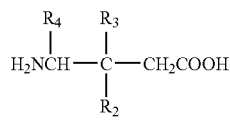

II hydrogen, methyl, or carboxyl; or an individual enantiomeric isomer thereof; or a pharmaceutically acceptable salt thereof, are useful in the treatment of insomnia (U.S. patent application Ser. No. 60/092,166 filed Jul. 9, 1998, which is incorporated here by reference).

SUMMARY OF THE INVENTION

The instant invention is a method of treating insomnia, that is, difficulty in sleeping or disturbed sleep patterns which leave the perception of insufficient sleep. Insomnia is a common symptom which may be due to several emotional and physical disorders (The Merck Manual, 16$^{th}$ ed., pp 1445–6).

The benefit of using compounds of the invention to treat insomnia is that they are not addictive. Additionally, they have a half-life in the body that is suitable to work during the evening and subsequently clear the body by morning to allow for easy arousal. The compounds can be combined with other agents to enhance the sleep inducing effects. Such agents include melatonin, tryptophan, valerian, passiflora, antihistamines such as diphenydramine hydrochloride or doxylamine succinate, benzodiazepines, and nonbenzodiazepines hypnotics.

Additional advantages of using the compounds of formula 1 and 1A in the present invention include the relatively nontoxic nature of the compounds, the ease of preparation, the fact that the compounds are well-tolerated, and the ease of IV administration of the drugs. The subjects treated with the method of the present invention are mamnnals, including humans.

The compounds useful in the practice of the invention are those of formulas 1 and 1A

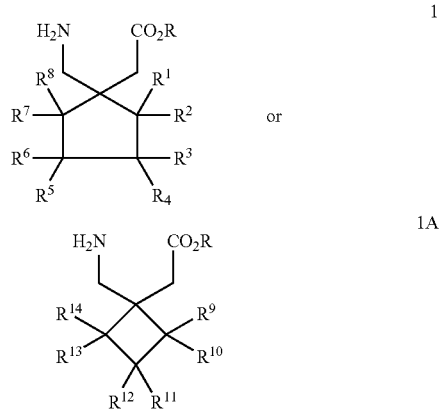

wherein R to $R^{14}$ are as defined below.

The compounds of the invention and their pharmaceutically acceptable salts and the prodrugs of the compounds are useful in the treatment of insomnia and sleeplessness.

DETAILED DESCRIPTION OF THE INVENTION

The compounds useful in the instant invention and their pharmaceutically acceptable salts are as defined by formulas 1 and 1A

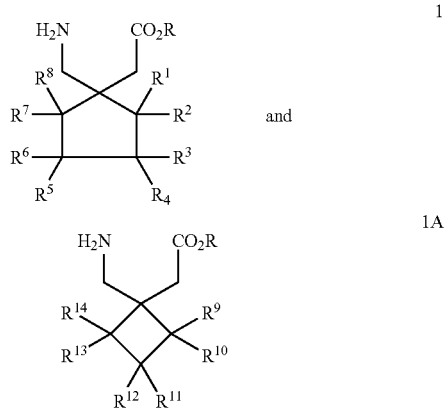

or a pharmaceutically acceptable salt thereof wherein:

R is hydrogen or a lower alkyl;

$R^1$ to $R^{14}$ are each independently selected from hydrogen, straight or branched alkyl of from 1 to 6 carbons, phenyl, benzyl, fluorine, chlorine, bromine, hydroxy, hydroxymethyl, amino, aminomethyl, trifluoromethyl, —$CO_2H$, —$CO_2R^{15}$, —$CH_2CO_2H$, —$CH_2CO_2R^{15}$, —$OR^{15}$ wherein $R^{15}$ is a straight or branched alkyl of from 1 to 6 carbons, phenyl, or benzyl, and $R^1$ to $R^8$ are not simultaneously hydrogen.

Preferred compounds of the invention are those of Formula I wherein $R^1$ to $R^{14}$ are selected from hydrogen, methyl, ethyl, propyl, isopropyl, butyl straight or branched, phenyl, or benzyl.

More preferred compounds are those of Formula I wherein $R^1$ to $R^{14}$ are selected from hydrogen, methyl, ethyl, or benzyl.

The most preferred compounds are selected from:

(1α,3α,4α)-(1-Aminomethyl-3,4-dimethyl-cyclopentyl)-acetic acid;

(1α,3α,4α)-(1-Aminomethyl-3,4-diethyl-cyclopentyl)-acetic acid;

(1α,3α,4α)-(1-Aminomethyl-3,4-diisopropyl-cyclopentyl)-acetic acid;

[1S-(1α,3α,4α)]-(1-Aminomethyl-3-ethyl-4-methyl-cyclopentyl)-acetic acid;

[1R-(1α,3α,4α)]-(1-Aminomethyl-3-ethyl-4-methyl-cyclopentyl)-acetic acid;

[1S-(1α,3α,4α)]-(1-Aminomethyl-3-isopropyl-4-methyl-cyclopentyl)-acetic acid;

[1R-(1α,3α,4α)]-(1-Aminomethyl-3-isopropyl-4-methyl-cyclopentyl)-acetic acid;

[1S-(1α,3α,4α)]-(1-Aminomethyl-3-ethyl-4-isopropyl-cyclopentyl)-acetic acid;

[1R-(1α,3α,4α)]-(1-Aminomethyl-3-ethyl-4-isopropyl-cyclopentyl)-acetic acid;

[1S-(1α,3α,4α)]-(1-Aminomethyl-3-tert-butyl-4-methyl-cyclopentyl)-acetic acid;

[1R-(1α,3α,4α)]-(1-Aminomethyl-3-tert-butyl-4-methyl-cyclopentyl)-acetic acid;

[1S-(1α,3α,4α)]-(1-Aminomethyl-3-tert-butyl-4-ethyl-cyclopentyl)-acetic acid;

[1R-(1α,3α,4α)]-(1-Aminomethyl-3-tert-butyl-4-ethyl-cyclopentyl)-acetic acid;

[1S-(1α,3α,4α)]-(1-Aminomethyl-3-tert-butyl-4-isopropyl-cyclopentyl)-acetic acid;

[1R-(1α,3α,4α)]-(1-Aminomethyl-3-tert-butyl-4-isopropyl-cyclopentyl)-acetic acid;

(1α,3α,4α)-(1-Aminomethyl-3,4-di-tert-butyl-cyclopentyl)-acetic acid;

[1S-(1α,3α,4α)]-(1-Aminomethyl-3-methyl-4-phenyl-cyclopentyl)-acetic acid;

[1R-(1α,3α,4α)]-(1-Aminomethyl-3-methyl-4-phenyl-cyclopentyl)-acetic acid;

[1S-(1α,3α,4α)]-(1-Aminomethyl-3-benzyl-4-methyl-cyclopentyl)-acetic acid;

[1R-(1 α,3α,4α)]-(1-Aminomethyl-3-benzyl-4-methyl-cyclopentyl)-acetic acid;

(1S-cis)-(1-Aminomethyl-3-methyl-cyclopentyl)-acetic acid;

(1S-cis)-(1-Aminomethyl-3-ethyl-cyclopentyl)-acetic acid;

(1S-cis)-(1-Aminomethyl-3-isopropyl-cyclopentyl)-acetic acid;

(1S-cis)-(1-Aminomethyl-3-tert-butyl-cyclopentyl)-acetic acid;

(1S-cis)-(1-Aminomethyl-3-phenyl-cyclopentyl)-acetic acid;

(1S-cis)-(1-Aminomethyl-3-benzyl-cyclopentyl)-acetic acid;

(1R-cis)-(1-Aminomethyl-3-methyl-cyclopentyl)-acetic acid;

(1R-cis)-(1-Aminomethyl-3-ethyl-cyclopentyl)-acetic acid;

(1R-cis)-(1-Aminomethyl-3-isopropyl-cyclopentyl)-acetic acid;

(1R-cis)-(1-Aminomethyl-3-tert-butyl-cyclopentyl)-acetic acid;

(1R-cis)-(1-Aminomethyl-3-phenyl-cyclopentyl)-acetic acid;

(1R-cis)-(1-Aminomethyl-3-benzyl-cyclopentyl)-acetic acid;

(S)-(1-Aminomethyl-3,3-dimethyl-cyclopentyl)-acetic acid;

(S)-(1-Aminomethyl-3,3-diethyl-cyclopentyl)-acetic acid;

(1-Aminomethyl-3,3,4,4-tetramethyl-cyclopentyl)-acetic acid;

(1-Aminomethyl-3,3,4,4-tetraethyl-cyclopentyl)-acetic acid;

(1α,3β,4β)-(1-Aminomethyl-3,4-dimethyl-cyclopentyl)-acetic acid;

(1α,3β,4β)-(1-Aminomethyl-3,4-diethyl-cyclopentyl)-acetic acid;

(1α,3β,4β)-(1-Aminomethyl-3,4-diisopropyl-cyclopentyl)-acetic acid;

[1R-(1α,3β,4β)]-(1-Aminomethyl-3-ethyl-4-methyl-cyclopentyl)-acetic acid;

[1S-(1α,3β,4β)]-(1-Aminomethyl-3-ethyl-4-methyl-cyclopentyl)-acetic acid;

[1R-(1α,3β,4β)]-(1-Aminomethyl-3-isopropyl-4-methyl-cyclopentyl)-acetic acid;

[1S-(1α,3β,4β)]-(1-Aminomethyl-3-isopropyl-4-methyl-cyclopentyl)-acetic acid;

[1R-(1α,3β,4β)]-(1-Aminomethyl-3-ethyl-4-isopropyl-cyclopentyl)-acetic acid;

[1S-(1α,3β,4β)]-(1-Aminomethyl-3-ethyl-4-isopropyl-cyclopentyl)-acetic acid;

[1R-(1α,3β,4β)]-(1-Aminomethyl-3-tert-butyl-4-methyl-cyclopentyl)-acetic acid;

[1S-(1α,3β,4β)]-(1-Aminomethyl-3-tert-butyl-4-methyl-cyclopentyl)-acetic acid;

[1R-(1α,3β,4β)]-(1-Aminomethyl-3-tert-butyl-4-ethyl-cyclopentyl)-acetic acid;

[1S-(1α,3β,4β)]-(1-Aminomethyl-3-tert-butyl-4-ethyl-cyclopentyl)-acetic acid;

[1R-(1α,3β,4β)]-(1-Aminomethyl-3-tert-butyl-4-isopropyl-cyclopentyl)-acetic acid;

[1S-(1α,3β,4β)]-(1-Aminomethyl-3-tert-butyl-4-isopropyl-cyclopentyl)-acetic acid;

(1α,3β,4β)-(1-Aminomethyl-3,4-di-tert-butyl-cyclopentyl)-acetic acid;

[1R-(1α,3β,4β)]-(1-Aminomethyl-3-methyl-4-phenyl-cyclopentyl)-acetic acid;

[1S-(1α,3β,4β)]-(1-Aminomethyl-3-methyl-4-phenyl-cyclopentyl)-acetic acid;

[1R-(1α,3β,4β)]-(1-Aminomethyl-3-benzyl-4-methyl-cyclopentyl)-acetic acid;

[1S-(1α,3β,4β)]-(1-Aminomethyl-3-benzyl-4-methyl-cyclopentyl)-acetic acid;

(1R-trans)-(1-Aminomethyl-3-methyl-cyclopentyl)-acetic acid;

(1R-trans)-(1-Aminomethyl-3-ethyl-cyclopentyl)-acetic acid;
(1R-trans)-(1-Aminomethyl-3-isopropyl-cyclopentyl)-acetic acid;
(1R-trans)-(1-Aminomethyl-3-tert-butyl-cyclopentyl)-acetic acid;
(1R-trans)-(1-Aminomethyl-3-phenyl-cyclopentyl)-acetic acid;
(1R-trans)-(1-Aminomethyl-3-benzyl-cyclopentyl)-acetic acid;
(1S-trans)-(1-Aminomethyl-3-methyl-cyclopentyl)-acetic acid;
(1S-trans)-(1-Aminomethyl-3-ethyl-cyclopentyl)-acetic acid;
(1S-trans)-(1-Aminomethyl-3-isopropyl-cyclopentyl)-acetic acid;
(1S-trans)-(1-Aminomethyl-3-tert-butyl-cyclopentyl)-acetic acid;
(1S-trans)-(1-Aminomethyl-3-phenyl-cyclopentyl)-acetic acid;
(1S-trans)-(1-Aminomethyl-3-benzyl-cyclopentyl)-acetic acid;
(R)-(1-Aminomethyl-3,3-dimethyl-cyclopentyl)-acetic acid;
(R)-(1-Aminomethyl-3,3-diethyl-cyclopentyl)-acetic acid;
cis-(1-Aminomethyl-3-methyl-cyclobutyl)-acetic acid;
cis-(1-Aminomethyl-3-ethyl-cyclobutyl)-acetic acid;
cis-(1-Aminomethyl-3-isopropyl-cyclobutyl)-acetic acid;
cis-(1-Aminomethyl-3-tert-butyl-cyclobutyl)-acetic acid;
cis-(1-Aminomethyl-3-phenyl-cyclobutyl)-acetic acid;
cis-(1-Aminomethyl-3-benzyl-cyclobutyl)-acetic acid;
trans-(1-Aminomethyl-3-methyl-cyclobutyl)-acetic acid;
trans-(1-Aminomethyl-3-ethyl-cyclobutyl)-acetic acid;
trans-(1-Aminomethyl-3-isopropyl-cyclobutyl)-acetic acid;
trans-(1-Aminomethyl-3-tert-butyl-cyclobutyl)-acetic acid;
trans-(1-Aminomethyl-3-phenyl-cyclobutyl)-acetic acid;
trans-(1-Aminomethyl-3-benzyl-cyclobutyl)-acetic acid;
cis-(1-Aminomethyl-3-ethyl-3-methyl-cyclobutyl)-acetic acid;
cis-(1-Aminomethyl-3-isopropyl-3-methyl-cyclobutyl)-acetic acid;
cis-(1-Aminomethyl-3-tert-butyl-3-methyl-cyclobutyl)-acetic acid;
cis-(1-Aminomethyl-3-methyl-3-phenyl-cyclobutyl)-acetic acid;
cis-(1-Aminomethyl-3-benzyl-3-methyl-cyclobutyl)-acetic acid;
trans-(1-Aminomethyl-3-ethyl-3-methyl-cyclobutyl)-acetic acid;
trans-(1-Aminomethyl-3-isopropyl-3-methyl-cyclobutyl)-acetic acid;
trans-(1-Aminomethyl-3-tert-butyl-3-methyl-cyclobutyl)-acetic acid;
trans-(1-Aminomethyl-3-methyl-3-phenyl-cyclobutyl)-acetic acid;
trans-(1-Aminomethyl-3-benzyl-3-methyl-cyclobutyl)-acetic acid;
cis-(1-Aminomethyl-3-ethyl-3-isopropyl-cyclobutyl)-acetic acid;
cis-(1-Aminomethyl-3-tert-butyl-3-ethyl-cyclobutyl)-acetic acid;
cis-(1-Aminomethyl-3-ethyl-3-phenyl-cyclobutyl)-acetic acid;
cis-(1-Aminomethyl-3-benzyl-3-ethyl-cyclobutyl)-acetic acid;
trans-(1-Aminomethyl-3-ethyl-3-isopropyl-cyclobutyl)-acetic acid;
trans-(1-Aminomethyl-3-tert-butyl-3-ethyl-cyclobutyl)-acetic acid;
trans-(1-Aminomethyl-3-ethyl-3-phenyl-cyclobutyl)-acetic acid;
trans-(1-Aminomethyl-3-benzyl-3-ethyl-cyclobutyl)-acetic acid;
cis-(1-Aminomethyl-3-tert-butyl-3-isopropyl-cyclobutyl)-acetic acid;
cis-(1-Aminomethyl-3-isopropyl-3-phenyl-cyclobutyl)-acetic acid;
trans-(1-Aminomethyl-3-benzyl-3-isopropyl-cyclobutyl)-acetic acid;
cis-(1-Aminomethyl-3-tert-butyl-3-phenyl-cyclobutyl)-acetic acid;
trans-(1-Aminomethyl-3-benzyl-3-tert-butyl-cyclobutyl)-acetic acid;
trans-(1-Aminomethyl-3-tert-butyl-3-isopropyl-cyclobutyl)-acetic acid;
trans-(1-Aminomethyl-3-isopropyl-3-phenyl-cyclobutyl)-acetic acid;
cis-(1-Aminomethyl-3-benzyl-3-isopropyl-cyclobutyl)-acetic acid;
trans-(1-Aminomethyl-3-tert-butyl-3-phenyl-cyclobutyl)-acetic acid;
cis-(1-Aminomethyl-3-benzyl-3-tert-butyl-cyclobutyl)-acetic acid;
(1-Aminomethyl-3,3-dimethyl-cyclobutyl)-acetic acid;
(1-Aminomethyl-3,3-diethyl-cyclobutyl)-acetic acid;
(1-Aminomethyl-3,3-diisopropyl-cyclobutyl)-acetic acid;
(1-Aminomethyl-3,3-di-tert-butyl-cyclobutyl)-acetic acid;
(1-Aminomethyl-3,3-diphenyl-cyclobutyl)-acetic acid;
(1-Aminomethyl-3,3-dibenzyl-cyclobutyl)-acetic acid;
(1-Aminomethyl-2,2,4,4-tetramethyl-cyclobutyl)-acetic acid;
(1-Aminomethyl-2,2,3,3,4,4-hexamethyl-cyclobutyl)-acetic acid;
(R)-(1-Aminomethyl-2,2-dimethyl-cyclobutyl)-acetic acid;
(S)-(1-Aminomethyl-2,2-dimethyl-cyclobutyl)-acetic acid;
(1R-cis)-(1-Aminomethyl-2-methyl-cyclobutyl)-acetic acid;
[1R-(1α,2α,3α)]-(1-Aminomethyl-2,3-dimethyl-cyclobutyl)-acetic acid;
(1α,2α,4α)-(1-Aminomethyl-2,4-dimethyl-cyclobutyl)-acetic acid;
[1R-(1α,2α,3β)]-(1-Aminomethyl-2,3-dimethyl-cyclobutyl)-acetic acid;
(1α,2α,4β)-(1-Aminomethyl-2,4-dimethyl-cyclobutyl)-acetic acid;
(1S-trans)-(1-Aminomethyl-2-methyl-cyclobutyl)-acetic acid;
[1S-(1α,2β,3β)]-(1-Aminomethyl-2,3-dimethyl-cyclobutyl)-acetic acid;
(1α,2β,4β)-(1-Aminomethyl-2,4-dimethyl-cyclobutyl)-acetic acid;
[1S-(1α,2β,3α)]-(1-Aminomethyl-2,3-dimethyl-cyclobutyl)-acetic acid;
(1α,2β,4α)-(1-Aminomethyl-2,4-dimethyl-cyclobutyl)-acetic acid;
(1R-trans)-(1-Aminomethyl-2-methyl-cyclobutyl)-acetic acid;

[1R-(1α,2β,3β)]-(1-Aminomethyl-2,3-dimethyl-cyclobutyl)-acetic acid;
[1R-(1α,2β,4β)]-(1-Aminomethyl-2-ethyl-4-methyl-cyclobutyl)-acetic acid;
[1R-(1α,2β,3α)]-(1-Aminomethyl-2,3-dimethyl-cyclobutyl)-acetic acid;
(1α,2β,4α)-(1-Aminomethyl-2,4-dimethyl-cyclobutyl)-acetic acid;
(1S-cis)-(1-Aminomethyl-2-methyl-cyclobutyl)-acetic acid;
[1S-(1α,2α,3α)]-(1-Aminomethyl-2,3-dimethyl-cyclobutyl)-acetic acid;
[1S-(1α,2α,3α)]-(1-Aminomethyl-2,4-dimethyl-cyclobutyl)-acetic acid;
[1S-(1α,2β,3α)]-(1-Aminomethyl-2,3-dimethyl-cyclobutyl)-acetic acid;
(1α,2α,4β)-(1-Aminomethyl-2,4-dimethyl-cyclobutyl)-acetic acid;
(3S,4S)-(1-Aminomethyl-3,4-dimethyl-cyclopentyl)-acetic acid;
(3R,4R)-(1-Aminomethyl-3,4-dimethyl-cyclopentyl)-acetic acid;
(3R,4R)-(1-Aminomethyl-3,4-diethyl-cyclopentyl)-acetic acid;
(3S,4S)-(1-Aminomethyl-3,4-diisopropyl-cyclopentyl)-acetic acid;
(3R,4R)-(1-Aminomethyl-3,4-diisopropyl-cyclopentyl)-acetic acid;
(3S,4S)-(1-Aminomethyl-3,4-di-tert-butyl-cyclopentyl)-acetic acid;
(3R,4R)-(1-Aminomethyl-3,4-di-tert-butyl-cyclopentyl)-acetic acid;
(3S,4S)-(1-Aminomethyl-3,4-diphenyl-cyclopentyl)-acetic acid;
(3R,4R)-(1-Aminomethyl-3,4-diphenyl-cyclopentyl)-acetic acid;
(3S,4S)-(1-Aminomethyl-3,4-dibenzyl-cyclopentyl)-acetic acid;
(3R,4R)-(1-Aminomethyl-3,4-dibenzyl-cyclopentyl)-acetic acid;
[1S-(1α,3α,4β)]1-(1-Aminomethyl-3-methyl-4-ethyl-cyclopentyl)-acetic acid;
[1R-(1α,3β,4α)]-(1-Aminomethyl-3-methyl-4-ethyl-cyclopentyl)-acetic acid;
[1R-(1α,3α,4β)]-(1-Aminomethyl-3-methyl-4-ethyl-cyclopentyl)-acetic acid;
[1S-(1α,3β,4α)]-(1-Aminomethyl-3-methyl-4-ethyl-cyclopentyl)-acetic acid;
[1S-(1α,3α,4β)]-(1-Aminomethyl-3-methyl-4-isopropyl-cyclopentyl)-acetic acid;
[1R-(1α,3β,4α)]-(1-Aminomethyl-3-methyl-4-isopropyl-cyclopentyl)-acetic acid;
[1R-(1α,3α,4β)]-(1-Aminomethyl-3-methyl-4-isopropyl-cyclopentyl)-acetic acid;
[1S-(1α,3β,4α)]-(1-Aminomethyl-3-methyl-4-isopropyl-cyclopentyl)-acetic acid;
[1S-(1α,3α,4β)]-(1-Aminomethyl-3-methyl-4-tert-butyl-cyclopentyl)-acetic acid;
[1R-(1α,3β,4α)]-(1-Aminomethyl-3-methyl-4-tert-butyl-cyclopentyl)-acetic acid;
[1R-(1α,3α,4β)]-(1-Aminomethyl-3-methyl-4-tert-butyl-cyclopentyl)-acetic acid;
[1S-(1α,3β,4α)]-(1-Aminomethyl-3-methyl-4-tert-butyl-cyclopentyl)-acetic acid;
[1S-(1α,3α,4β)]-(1-Aminomethyl-3-methyl-4-phenyl-cyclopentyl)-acetic acid;
[1R-(1α,3β,4α)]-(1-Aminomethyl-3-methyl-4-phenyl-cyclopentyl)-acetic acid;
[1R-(1α,3β,4α)]-(1-Aminomethyl-3-methyl-4-phenyl-cyclopentyl)-acetic acid;
[1S-(1α,3β,4α)]-(1-Aminomethyl-3-methyl-4-phenyl-cyclopentyl)-acetic acid;
[1S-(1α,3α,4β)]-(1-Aminomethyl-3-benzyl-4-methyl-cyclopentyl)-acetic acid;
[1R-(1α,3β,4α)]-(1-Aminomethyl-3-benzyl-4-methyl-cyclopentyl)-acetic acid;
[1R-(1α,3α,4β)]-(1-Aminomethyl-3-benzyl-4-methyl-cyclopentyl)-acetic acid;
[1S-(1α,3β,4α)]-(1-Aminomethyl-3-benzyl-4-methyl-cyclopentyl)-acetic acid;
[1S-(1α,3α,4β)]-(1-Aminomethyl-3-ethyl-4-isopropyl-cyclopentyl)-acetic acid;
[1R-(1α,3β,4α)]-(1-Aminomethyl-3-ethyl-4-isopropyl-cyclopentyl)-acetic acid;
[1R-(1α,3α,4β)]-(1-Aminomethyl-3-ethyl-4-isopropyl-cyclopentyl)-acetic acid;
[1S-(1α,3β,4α)]-(1-Aminomethyl-3-ethyl-4-isopropyl-cyclopentyl)-acetic acid;
[1S-(1α,3α,4β)]-(1-Aminomethyl-3-tert-butyl-4-ethyl-cyclopentyl)-acetic acid;
[1R-(1α,3β,4α)]-(1-Aminomethyl-3-tert-butyl-4-ethyl-cyclopentyl)-acetic acid;
[1R-(1α,3α,4β)]-(1-Aminomethyl-3-tert-butyl-4-ethyl-cyclopentyl)-acetic acid;
[1S-(1α,3β,4α)]-(1-Aminomethyl-3-tert-butyl-4-ethyl-cyclopentyl)-acetic acid;
[1S-(1α,3α,4β)]-(1-Aminomethyl-3-ethyl-4-phenyl-cyclopentyl)-acetic acid;
[1R-(1α,3β,4α)]-(1-Aminomethyl-3-ethyl-4-phenyl-cyclopentyl)-acetic acid;
[1R-(1α,3α,4β)]-(1-Aminomethyl-3-ethyl-4-phenyl-cyclopentyl)-acetic acid;
[1S-(1α,3β,4α)]-(1-Aminomethyl-3-ethyl-4-phenyl-cyclopentyl)-acetic acid;
[1S-(1α,3α,4β)]-(1-Aminomethyl-3-benzyl-4-ethyl-cyclopentyl)-acetic acid;
[1R-(1α,3β,4α)]-(1-Aminomethyl-3-benzyl-4-ethyl-cyclopentyl)-acetic acid;
[1R-(1α,3α,4β)]-(1-Aminomethyl-3-benzyl-4-ethyl-cyclopentyl)-acetic acid;
[1S-(1α,3β,4α)]-(1-Aminomethyl-3-benzyl-4-ethyl-cyclopentyl)-acetic acid;
[1S-(1α,3α,4β)]-(1-Aminomethyl-3-tert-butyl-4-isopropyl-cyclopentyl)-acetic acid;
[1R-(1α,3β,4α)]-(1-Aminomethyl-3-tert-butyl-4-isopropyl-cyclopentyl)-acetic acid;
[1R-(1α,3α,4β)]-(1-Aminomethyl-3-tert-butyl-4-isopropyl-cyclopentyl)-acetic acid;
[1S-(1α,3β,4α)]-(1-Aminomethyl-3-tert-butyl-4-isopropyl-cyclopentyl)-acetic acid;
[1S-(1α,3α,4β)]-(1-Aminomethyl-3-isopropyl-4-phenyl-cyclopentyl)-acetic acid;
[1R-(1α,3β,4α)]-(1-Aminomethyl-3-isopropyl-4-phenyl-cyclopentyl)-acetic acid;
[1R-(1α,3α,4β)]-(1-Aminomethyl-3-isopropyl-4-phenyl-cyclopentyl)-acetic acid;
[1S-(1α,3β,4α)]-(1-Aminomethyl-3-isopropyl-4-phenyl-cyclopentyl)-acetic acid;
[1S-(1α,3α, 4β)]-(1-Aminomethyl-3-benzyl-4-isopropyl-cyclopentyl)-acetic acid;
[1R-(1α,3β,4α)]-(1-Aminomethyl-3-benzyl-4-isopropyl-cyclopentyl)-acetic acid;

[1R-(1α,3α,4β)]-(1-Aminomethyl-3-benzyl-4-isopropyl-cyclopentyl)-acetic acid;
[1S-(1α,3β,4α)]-(1-Aminomethyl-3-benzyl-4-isopropyl-cyclopentyl)-acetic acid;
[1S-(1α,3α,4β)]-(1-Aminomethyl-3-tert-butyl-4-phenyl-cyclopentyl)-acetic acid;
[1R-(1α,3β,4α)]-(1-Aminomethyl-3-tert-butyl-4-phenyl-cyclopentyl)-acetic acid;
[1R-(1α,3α,4β)]-(1-Aminomethyl-3-tert-butyl-4-phenyl-cyclopentyl)-acetic acid;
[1S-(1α,3β,4α)]-(1-Aminomethyl-3-tert-butyl-4-phenyl-cyclopentyl)-acetic acid;
[1R-(1α,3α,4β)]-(1-Aminomethyl-3-benzyl-4-tert-butyl-cyclopentyl)-acetic acid;
[1S-(1α,3β,4α)]-(1-Aminomethyl-3-benzyl-4-tert-butyl-cyclopentyl)-acetic acid;
[1S-(1α,3α,4β)]-(1-Aminomethyl-3-benzyl-4-tert-butyl-cyclopentyl)-acetic acid;
[1R-(1α,3β,4α)]-(1-Aminomethyl-3-benzyl-4-tert-butyl-cyclopentyl)-acetic acid;
[1S-(1α,3α,4β)]-(1-Aminomethyl-3-benzyl-4-phenyl-cyclopentyl)-acetic acid;
[1R-(1α,3β,4α)]-(1-Aminomethyl-3-benzyl-4-phenyl-cyclopentyl)-acetic acid;
[1R-(1α,3α,4β)]-(1-Aminomethyl-3-benzyl-4-phenyl-cyclopentyl)-acetic acid;
[1S-(1α,3β,4α)]-(1-Aminomethyl-3-benzyl-4-phenyl-cyclopentyl)-acetic acid;
(1R-cis)-(1-Aminomethyl-2-methyl-cyclopentyl)-acetic acid;
(1S-cis)-(1-Aminomethyl-2-methyl-cyclopentyl)-acetic acid;
(1R-trans)-(1-Aminomethyl-2-methyl-cyclopentyl)-acetic acid;
(1S-trans)-(1-Aminomethyl-2-methyl-cyclopentyl)-acetic acid;
(R)-(1-Aminomethyl-2,2-dimethyl-cyclopentyl)-acetic acid;
(S)-(1-Aminomethyl-2,2-dimethyl-cyclopentyl)-acetic acid;
(1-Aminomethyl-2,2,5,5-tetramethyl-cyclopentyl)-acetic acid;
(1α,2β,5β)-(1-Aminomethyl-2,5-dimethyl-cyclopentyl)-acetic acid;
(2R, 5R)-(1-Aminomethyl-2,5-dimethyl-cyclopentyl)-acetic acid;
(2S, 5S)-(1-Aminomethyl-2,5-dimethyl-cyclopentyl)-acetic acid;
(1α,2α,5α)-(1-Aminomethyl-2,5-dimethyl-cyclopentyl)-acetic acid;
[1R-(1α,2α,3α)]-(1-Aminomethyl-2,3-dimethyl-cyclopentyl)-acetic acid;
[1R-(1α,2β,3α)]-(1-Aminomethyl-2,3-dimethyl-cyclopentyl)-acetic acid;
[1R-(1α,2α,3β)]-(1-Aminomethyl-2,3-dimethyl-cyclopentyl)-acetic acid;
[1R-(1α,2β,3β)]-(1-Aminomethyl-2,3-dimethyl-cyclopentyl)-acetic acid;
[1S-(1α,2α, 3α)]-(1-Aminomethyl-2,3-dimethyl-cyclopentyl)-acetic acid;
[1S-(1α,2β,3α)]-(1-Aminomethyl-2,3-dimethyl-cyclopentyl)-acetic acid;
[1S-(1α,2α,3β)]-(1-Aminomethyl-2,3-dimethyl-cyclopentyl)-acetic acid;
[1S-(1α,2β,3β)]-(1-Aminomethyl-2,3-dimethyl-cyclopentyl)-acetic acid;
[1R-(1α,2α,4α)]-(1-Aminomethyl-2,4-dimethyl-cyclopentyl)-acetic acid;
[1S-(1α,2α,4α)]-(1-Aminomethyl-2,4-dimethyl-cyclopentyl)-acetic acid;
[1R-(1α,2α,4β)]-(1-Aminomethyl-2,4-dimethyl-cyclopentyl)-acetic acid;
[1S-(1α,2α,4β)]-(1-Aminomethyl-2,4-dimethyl-cyclopentyl)-acetic acid;
[1R-(1α,2β,4α)]-(1-Aminomethyl-2,4-dimethyl-cyclopentyl)-acetic acid;
[1S-(1α,2β,4α)]-(1-Aminomethyl-2,4-dimethyl-cyclopentyl)-acetic acid;
[1R-(1α,2β,4β)]-(1-Aminomethyl-2,4-dimethyl-cyclopentyl)-acetic acid; and
1 S-(1α,2β,4β)]-(1-Aminomethyl-2,4-dimethyl-cyclopentyl)-acetic acid.

Especially useful as an agent for insomnia and related disorders is (3S, 4S)-(1-Aminomethyl-3,4-dimethyl-cyclopentyl)-acetic acid.

Also, especially useful as an agent for insomnia and related disorders is (3S, 5R)-3-Aminomethyl-5-methyl-octanoic acid.

The term "lower alkyl" is a straight or branched group of from 1 to 4 carbons.

The term "alkyl" is a straight or branched group of from 1 to 6 carbon atoms including but not limited to methyl, ethyl, propyl, n-propyl, isopropyl, butyl, 2-butyl, tert-butyl, pentyl, except as where otherwise stated.

The benzyl and phenyl groups may be unsubstituted or substituted by from 1 to 3 substituents selected from hydroxy, carboxy, carboalkoxy, halogen, $CF_3$, nitro, alkyl, and alkoxy. Preferred are halogens.

Since amino acids are amphoteric, pharmacologically compatible salts when R is hydrogen can be salts of appropriate inorganic or organic acids, for example, hydrochloric, sulphuric, phosphoric, acetic, oxalic, lactic, citric, malic, salicylic, malonic, maleic, succinic, methanesulfonic acid, and ascorbic. Starting from corresponding hydroxides or carbonates, salts with alkali metals or alkaline earth metals, for example, sodium, potassium, magnesium, or calcium are formed. Salts with quaternary ammonium ions can also be prepared with, for example, the tetramethyl-ammonium ion. The carboxyl group of the amino acids can be esterified by known means.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

Methods and Materials

Methods

Male Sprague-Dawley rats weighing 250 to 360 g were used for the experiment. The rats were kept on a 12:12-hr light/dark cycle (lights on at 0900) at 23±1° C. ambient temperature. They had free access water and food during the experiment. Stainless steel jewelry screws for EEG recording were placed over the frontal and parietal cortices. An EMG electrode was implanted in the dorsal neck muscles.

Recording and analyses. After the recovery period (at least 1 week), rats were moved to sleep recording chambers. The rats were allowed relatively unrestricted movement inside the recording cages. A flexible tether connected the electrodes led to an electronic swivel. The leads from the swivel were routed to Grass Model No. 7D polygraphs in an adjacent room for recording EEG and EMG activity. The vigilance states of wakefulness, nonrapid-eye-movement sleep (NREMS), and rapid-eye-movement sleep (REMS) were determined offline in 10 second epochs. The amount of time spent in each vigilance state was calculated every hour and totaled for the 12-hour period post injection. Drug or vehicle were administered PO just prior to the onset of the light phase of the rat's light/dark cycle. Each rat received a vehicle and one drug dose.

Results (3S,4S)-1-Aminomethyl-3,4-dimethyl-cyclopentyl)-acetic acid (Compound 1), 3, 10, and 30 mg/kg PO and (3S,5R)-3-Aminomethyl-5-methyl-octanoic acid (Compound 2), 1, 3, and 20 mg/kg PO significantly increased NREMS in rats during the 12-hour period following injection (Table 1 and Table 2, respectively). This increase in NREMS sleep in rats is the typical profile demonstrated by agents that are used as sleep-inducing agents in humans (Meltzer L. T. and Serpa K. A., Assessment of hypnotic effects in the rat: Influence of the sleep-awake cycle, *Drug Development Research* 1988;14:151–159; Depoortere H. et al., Hypnotics: Clinical value of pharmaco-EEG methods, *Neuropsychobiology* 1986;16:157–162).

TABLE 1

Compound 1 Increases NREMS Sleep in Rats (N = 8/Treatment)

| Compound 1 (mg/kg PO) | Total Minutes (Mean ± SEM) NREMS for 12-Hour Postinjection | |
| --- | --- | --- |
| | Vehicle | Drug |
| 3 | 370 ± 11 | 401 ± 8* |
| 10 | 383 ± 8 | 409 ± 12* |
| 30 | 371 ± 14 | 424 ± 6* |

*$P \leq 0.05$ vs Vehicle (paired t-test)

TABLE 2

Compound 2 Increases NREMS Sleep in Rats (N = 8/Treatment)

| Compound 2 (mg/kg PO) | Total Minutes (Mean ± SEM) NREMS for 12-Hour Postinjection | |
| --- | --- | --- |
| | Vehicle | Drug |
| 1 | 409 ± 8 | 432 ± 8* |
| 3 | 406 ± 9 | 451 ± 9* |
| 10 | 412 ± 6 | 481 ± 6* |

*$P \leq 0.05$ vs Vehicle (paired t-test)

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of formula 1 or 1A or a corresponding pharmaceutically acceptable salt of a compound of formula 1 or 1A.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted, and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The invention claimed is:

1. A method of treating insomnia in a mammal in need of said treatment comprising administering a therapeutically effective amount of (3S, 4S)-1-Aminomethyl-3,4-dimethyl-cyclopentyl)-acetic acid or a pharmaceutically acceptable salt thereof.

2. A method of treating insomnia in a mammal in need of said treatment comprising administering a pharmaceutical composition comprising a therapeutically effective amount of (3S, 4S)-1-Aminomethyl-3,4-dimethyl-cyclopentyl)-acetic acid or a pharmaceutically acceptable salt thereof, and a pharmaceutically acceptable carrier.

3. The method of claim 2, wherein said composition comprises one active ingredient, wherein said active ingredient is (3S, 4S)-1-Aminomethyl-3,4-dimethyl-cyclopentyl)-acetic acid or a pharmaceutically acceptable salt thereof.

* * * * *